United States Patent
De La Mora et al.

(10) Patent No.: US 6,787,763 B2
(45) Date of Patent: Sep. 7, 2004

(54) METHOD AND APPARATUS TO INCREASE THE RESOLUTION AND WIDEN THE RANGE OF DIFFERENTIAL MOBILITY ANALYZERS (DMAS)

(76) Inventors: Juan Fernandez De La Mora, 80 Cold Spring St., New Haven, CT (US) 06511; Michael J. Labowsky, 5 Highview Ct., Wayne, NJ (US) 07470

( * ) Notice: Subject to any disclaimer, the term of this patent is extended or adjusted under 35 U.S.C. 154(b) by 0 days.

(21) Appl. No.: 10/286,672

(22) Filed: Nov. 1, 2002

(65) Prior Publication Data

US 2003/0116708 A1 Jun. 26, 2003

Related U.S. Application Data

(60) Provisional application No. 60/324,143, filed on Nov. 2, 2001.

(51) Int. Cl.⁷ .......................... H01J 49/40; G01N 27/60
(52) U.S. Cl. ...................... 250/287; 250/288; 73/28.04; 73/865.5; 324/452
(58) Field of Search ................................ 250/287, 288; 73/28.04, 865, 865.5; 324/452

(56) References Cited

U.S. PATENT DOCUMENTS

| | | | | |
|---|---|---|---|---|
| 5,218,203 A | * | 6/1993 | Eisele et al. | 250/288 |
| 5,596,136 A | * | 1/1997 | Flagan et al. | 73/28.04 |
| 5,869,831 A | * | 2/1999 | De La Mora et al. | 250/288 |
| 5,936,242 A | | 8/1999 | De La Mora et al. | |

OTHER PUBLICATIONS

Numerical Modeling Of The Performance Of Differential Mobility Analyzers For Nanometer Aerosol Measurements, Da–Ren Chen, et al., Journal of Aerosol Science, vol. 28, No. 6, pp. 985–1004, 1997.

High Resolution Size Analysis of Nanoparticles And Ions: Running A Vienna DMA of Near Optimal Length At Reynolds Numbers Up to 5000, L. de Juan, et al., Journal of Aerosol Science, vol. 29, No. 5/6, pp. 617–626, 1998.

Diffusion Broadening In Converging Differential Mobility Analyzers, J. Fernandez de la Mora, Journal of Aerosol Science, vol. 33, pp. 411–437, 2002.

Improvement Of The Resolution of TSI's 3071 DMA Via Redesigned Sheath Air and Aerosol Inlets, T. Eichler, et al., Aerosol Science and Technology, vol. 29, No. 1, pp. 39–49, Jul. 1998.

Electrospray Ionization For Mass Spectrometry of Large Biomolecules, John B. Fenn, et al., Science, vol. 246, pp. 64–71, Oct. 1989.

Differential Mobility Analysis Of Molecular Ions and Nanometer Particles, J. Fernandez de la Mora, Trends In Analytical Chemistry, vol. 17, No. 6, pp. 328–339, 1998.

Turbulent Transition Arises At Re—35,000 In A Short Vienna–Type DMA With A Large Laminarizing Inlet (Abstract Only), W. Herrmann, et al., AAAR 2000, 19$^{th}$ Annual AAAR Conference, Nov. 2000, pp. 499.

Macromolecule Analysis Based On Electrophoretic Mobility In Air: Globular Proteins, Stanley L. Kaufman, et al., Analytical Chemistry, vol. 68, No. 11, Jun. 1996.

Measurement of the Mobility Distribution of Tropospheric Ions, W. A. Hoppel, Pure and Applied Geophysics, vol. 81, pp. 230–245, 1970.

Laser Desorption Ionization of Proteins With Molecular Masses Exceeding 10,000 Daltons, Karas, et al., Analytical Chemistry, vol. 60, No. 20, pp. 2299–2301, Oct. 1988.

(List continued on next page.)

Primary Examiner—Jack Berman
(74) Attorney, Agent, or Firm—Carmody & Torrance LLP

(57) ABSTRACT

A differential mobility analyzer (DMA) for separating charged particles or ions suspended in a gas and a method of using the DMA for separating such particles. The invention includes various means for increasing the resolution of the DMA by stabilizing the laminar flow within the DMA and by allowing unusually large flow velocities.

83 Claims, 3 Drawing Sheets

OTHER PUBLICATIONS

Effect of Brownian Diffusion on Electrical Classification of Ultrafine Aerosol Particles In Differential Mobility Analyzer, Yasuo Kousaka, et al., Journal of Chemical Engineering of Japan, vol. 19, No. 5, pp. 401–407, 1986.

Minimization Of The Diffusive Broadening of Ultrafine Particles in Differential Mobility Analyzers, J. Rosell–Llompart, et al., Proceedings of the International Workshop on the Synthesis and Measurement of Ultrafine Particles, pp. 109–115, May 1993.

Sizing Nanoparticles And Ions With A Short Differential Mobility Analyzer, J. Rosell–Llompart, et al., Journal of Aerosol Science, vol. 27, No. 5, pp 695–719, 1996.

Size Distribution Measurement of Nanometer–Sized Aerosol Particles Using DMA Under Low–Pressure Conditions, Journal of Aerosol Science, vol. 28, No. 2, pp. 193–206, 1997.

* cited by examiner

METHOD AND APPARATUS TO INCREASE THE RESOLUTION AND WIDEN THE RANGE OF DIFFERENTIAL MOBILITY ANALYZERS (DMAS)

CROSS REFERENCE TO RELATED APPLICATION

This application claims the benefit of priority to U.S. Provisional Patent Application No. 60/324,143, filed on Nov. 2, 2001.

FIELD OF THE INVENTION

The invention relates to a method and apparatus for sizing and classifying charged particle or ions in a differential mobility analyzer.

BACKGROUND OF THE INVENTION

Differential mobility analyzers (DMAs) are the most powerful instruments available for sizing and classifying particles, especially in the diameter range below 100 nanometers. The most common DMA design involves two concentric cylindrical electrodes. The commercial versions of various instruments have served rather well the aerosol community's for several decades. A number of cylindrical designs have been studied, with different ratios between the electrode radii $R_1$ and $R_2$ and the axial distance L between inlet and outer slits for the aerosol flow. Other geometrical variations upstream the inlet or downstream the outlet slits have been tested for special purposes such as reducing the particle losses or the pressure drop, or for improving flow laminarity at moderate Reynolds number or to reach unusually high Reynolds numbers. As is well known to those skilled in the art, the Reynolds number is a dimensionless number which is equal to the density of a fluid times its velocity times a characteristic length, divided by the fluid's viscosity coefficient.

DMAs are used to separate small charged particles suspended in a gas according to their electrical mobility Z. They combine particle-free fluid flow (the sheath gas) and electric fields to drive charged particles introduced through a first narrow slit (the inlet or injection slit) located in a first electrode into a second narrow slit located in a second electrode. The space between these two slits and electrodes will be referred to as the "working section" of the DMA. Ideally, among the particles introduced through the injection slit, only those with mobilities contained within a relatively small range $\Delta Z$ centered about a mean value Z are sampled through the outlet slit. The inverse of the ratio $\Delta Z/Z$ is a measure of the DMA resolution. Traditionally, DMAs have been used for the separation of particles considerably larger than 5 nanometers. However, developments over the last decade have made these instruments suitable also for the separation of particles a few nanometers in diameter, and even smaller ions. Their use in the analysis of suspended ions and macroions is therefore of considerable practical interest. Such applications would benefit from the development of instruments of higher resolution and wider range than those that have been traditionally available. It should be noted that the term ion, as used in the instant application, refers not only to molecular ions, but also to charged clusters and in general to any charged particle.

The main obstacle limiting DMA resolution in the nanometer diameter range is Brownian motion. It is known that the associated peak broadening can be reduced considerably by two different means: (a) a geometrical design taking advantage of the existence of an optimal relative positioning between the two slits, and (b) increasing the Reynolds number (Re) of laminar operation of the sheath gas flow in the DMA to values as large as possible. Rosell-Llompart et al., Minimization of the diffusive broadening of ultrafine particles in differential mobility analyzers, in Synthesis and Characterization of Ultrafine Particles, pp. 109–114 (1993), the subject matter of which is herein incorporated by reference in its entirety, discloses high Reynolds number formulation accounting only for Brownian diffusion broadening in cylindrical DMAs. The relative full width $\Delta Z/Z$ of the mobility peak associated to particles of fixed mobility Z can be written as $$(\Delta Z/Z)^2 = 16\ln 2 D/(L^* U)(b+1/b); \qquad (1)$$

$$b = L/L^*; \quad L^{*2} = (R_2^2 - R_1^2)^2/[2(R_2^2 + R_1^2)]. \qquad (2,3)$$

D is the diffusivity of the particles, related to their electrical mobility Z via $$Z = De/(kT), \qquad (4)$$

whore e is the elementary charge (the particles are taken to be singly charged), k Boltzmann's constant and T the absolute temperature. $R_1$ and $R_2$ are the radii of the inner and outer cylindrical electrodes. L is the axial distance between the $_1$inlet and outlet slits, and U is the fluid velocity, taken to be independent of the radial coordinate r (plug flow). Suitable generalizations exist of these results for other velocity profiles, plane geometries, and even converging two-dimensional or axisymmetric situations. But equations (1–3) are representative of such broader cases, and suffice for the purposes of the present discussion. Since $(b+1/b) \geq 2$, it is clear that, at given radii $R_1$ and $R_2$ and fixed speed U, the resolution is maximized when the length L is equal to $L^*$. The advantages of using DMAs of near-optimal length were first demonstrated experimentally by Rosell-Llompart et al. (1993).

The need to use very high Reynolds numbers follows also immediately from (1). $L^*$ coincides with the width $\Delta = R_2 - R_1$ of the working section in the limit of a small gap, $\Delta \ll R_2$ (when $R_1$ tends to $R_2$), and is reasonably close to it even if $R_1/R_2$ differs substantially from unity ($L^*/\Delta = 0.843$ when $R_1/R_2 = 0.222$). Hence, the ratio $D/(L^* U)$ is fairly close to the Peclet number defined here as $$Pe = D/(\Delta U).$$

For the purposes of separating efficiently small species according to their mobility, it is desirable that $\Delta Z/Z$ be as small as 1%, even for ions with diameters as small as 1 or 2 nanometers. Since $(b+1/b) \geq 2$, this requirement implies that $L^* U/D > 2.22 \times 10^5$. Note also that small ions in standard air have mobilities of 2 cm$^2$/V/s, with associated diffusivities D=0.05 cm$^2$/s. The dimensionless ratio between the kinematic viscosity of air v (=0.15 cm$^2$/s) and D is therefore v/D=3, and the quantity $UL^*/v$ (close to the Reynolds number Re=$U\Delta/v$) needs then to be as high as $0.74 \times 10^5$. We shall see that, in order to cover a wide range of particle sizes, it is convenient to use DMAs with a distance L between the inlet and outlet slits as large as $3L^*$ or even larger (b>3), in which case the resolution is reduced by a factor $[(b+1/b)/2]^{1/2}$. To compensate for this effect calls for Reynolds numbers (Re) in excess of $10^5$.

The need for high Reynolds (or Peclet) numbers to moderate diffusion in convective diffusive flows is well known. However, the practical exploitation of this knowledge is made difficult by the natural tendency of high Reynolds number flows to become turbulent, as well as by the difficulties associated to the generation of the rather large flows required. For instance, Rosell, J., I. G. Loscertales D Bingham and J. Femández de la Mora "Sizing nanoparticles and ions with short differential mobility analyzer", J. Aerosol Science, 27. 695–719, 1996, have demonstrated an ability to reach Reynolds numbers as large as 5000 in a variant of the widely used DMA disclosed by Winklmair, et al., A New Electro-mobility Spectrometer for the Measurement of Aerosol Size Distributions in the Size Range from 1 to 1,000 nanometers, J. Aersol Sci., Vol. 22, pp. 289–296 (1991), (commonly referred to as the "Vienna DMA"). But they needed flow rates of some 800 liters/minute, with associated pressure drops close to half an atmosphere. Under such conditions it would have been rather difficult to attain the desired range of Reynolds numbers up to $10^5$.

Some important aspects of the problem of achieving high Reynolds numbers, while avoiding turbulent transition, have been addressed in U.S. Pat. No. 5,869,831 and U.S. Pat. No. 5,936,242, both to de la Mora, et al., the subject matter of which are herein incorporated by reference in their entirety, following the method of greatly reducing the level of perturbations in the inlet sheath gas flow by means of several stages of laminarizing screens and filters followed by a large contraction which accelerates substantially the sheath gas prior to the working section. For brevity, this large inlet contraction will be referred to as the "trumpet", even in non-axisymmetric designs.

Some additional clarifications are required here on the various means available to delay transition to relatively high Reynolds numbers. It is well known, that fully developed parabolic flow inside a tube tends to become turbulent at a critical Reynolds number near 2000, and that this critical value can be increased greatly when the inlet flow is carefully freed from velocity fluctuations. Often, the velocity profile at the entry of the working section is far closer to flat than parabolic, and this profile is less unstable than the parabolic flow. Still, the boundary layers forming near the cylindrical electrode walls tend also to become turbulent, and the critical conditions at which this happens are also pushed to considerably larger Reynolds numbers by a highly laminar inlet flow. Even so, transition eventually occurs. Furthermore, even in the most carefully prepared laminarizing system, it is very difficult to avoid all external sources of velocity fluctuations. And even when the fluctuation level of the entering flow is very small, local perturbations will tend to appear in the unstable mixing layer following the aerosol inlet. This last difficulty is addressed in the Vienna DMA by a slight reduction in the DMA cross section immediately after the inlet slit, which tends to stabilize the flow. However, this feature is meant to stabilize flows at Reynolds numbers well below 2000, and is likely to be ineffective at $Re=10^5$. A recent study of a variant of the Vienna DMA supplied with the very large inlet trumpet introduced in U.S. Pat. No. 5,869,831 observes turbulent transition at Re near 35,000. The boundary layers over their cylindrical electrodes evolve nearly as that over a flat plate, for which comparable conditions for transition are observed in an incoming stream with a velocity fluctuation level of the order of 1%. In contrast, free stream turbulence levels some 100 times smaller are required to achieve critical Reynolds numbers in the range $10^5$–$10^6$ in non-converging geometries. These observations indicate that, in planar or cylindrical DMAs, neither the large trumpet inlet proposed in U.S. Pat. No. 5,869,831, nor the slight acceleration used following the inlet slit of the Vienna DMA suffice to create laminar flows in the desired range $Re=10^5$.

SUMMARY OF THE INVENTION

The present invention comprises a method and apparatus for separating charged particles or ions in a differential mobility analyzer, wherein a stream of charge d particles or ions is introduced into an upstream portion of an analyzing region through an inlet slit, and wherein a combination of a laminar flow field and an electrical field leads to ions separating, comprising the steps of:

(a) introducing a stream of charged particles or ions of various electrical mobilities into said analyzing region;

(b) laminarizing a flow of a particle-free sheath gas, and introducing said sheath gas into said differential mobility analyzer immediately upstream of said analyzing region;

(c) maintaining the flow of said sheath gas within said analyzing region as laminar flow;

(d) providing an electrical field in said differential mobility analyzer, said electrical field being produced by a combination of electrodes and grids charged to various voltages and charging devices to maintain said electrodes and grids at said various voltages; and (e) sampling or collecting said separated particles or ions within a narrow range of electrical mobilities through at least one collector device.

In accordance with the preferred embodiment of the apparatus, the differential mobility analyzer for separating ions and charged particles suspended in a mixture comprises:

means to provide a laminar flow of ion-free sheath gas into an upstream end of an analyzing region at a Reynolds number in excess of 2000;

ion supply means for introducing said ions and charged particles into said analyzing region;

at least two electrodes charged to suitable potentials to create an electric field within said analyzing region;

whereby said ions are separated in space by combined action of the eletric field and the flow of sheath gas;

at least one sampling or collecting device, wherein ions of a desired mobility are sampled or collected;

power supply means to charge said at least two electrodes to said ptoentials;

means for maintaining said laminar flow within said analyzing region; and means to maintain flow spatial symmetry in the anlyzing region while minimizing pressure drop.

DETAILED DESCRIPTION OF THE PREFERRED EMBODIMENTS OF THE INVENTION

The instant invention comprises a method to keep the flow laminar at Reynolds numbers (Re) well above 35,000, the maximum value at which a carefully prepared DMA flow (with a large inlet trumpet) between cylinders or parallel plates has been previously seen to remain laminar. The new method stabilizes the flow by accelerating it. This feature is discussed in de la Mora, de la Mora, Diffusion Broadening in Converging Mobility Analyzers, J. Aerosol Science, Vol. 33, pp. 411–437 (2002), the subject matter of which is herein incorporated by reference in its entirety.

Generally, the present invention enables for the first time the attainment of high Reynolds numbers in excess of $10^5$ under laminar conditions, and, with the improvements discussed below, further enables the construction of DMAs capable of $\Delta Z/Z$ (based on the full peak width at half height, FWHH) values as small as 0.01, even for particles with diameters smaller than 2 nanometers.

Another aspect of this invention overcomes the problem of high losses at the inlet of cylindrical DMAs in the case of initially neutral species, such as drugs and explosives, by charging them immediately upstream of the inlet slit.

Still another aspect of this invention overcomes the prior incompatibility between short DMAs capable of high resolution in the nanometer size range, and long DMAs, capable of analyzing particles as large as 30 to 100 nanometers, including the means to make axisymmetric DMAs capable of high resolution analysis of particles at $\Delta Z/Z$ values of 1% over the full diameter range from 2 nanometers up to 30 nanometers and beyond.

Figure 1:
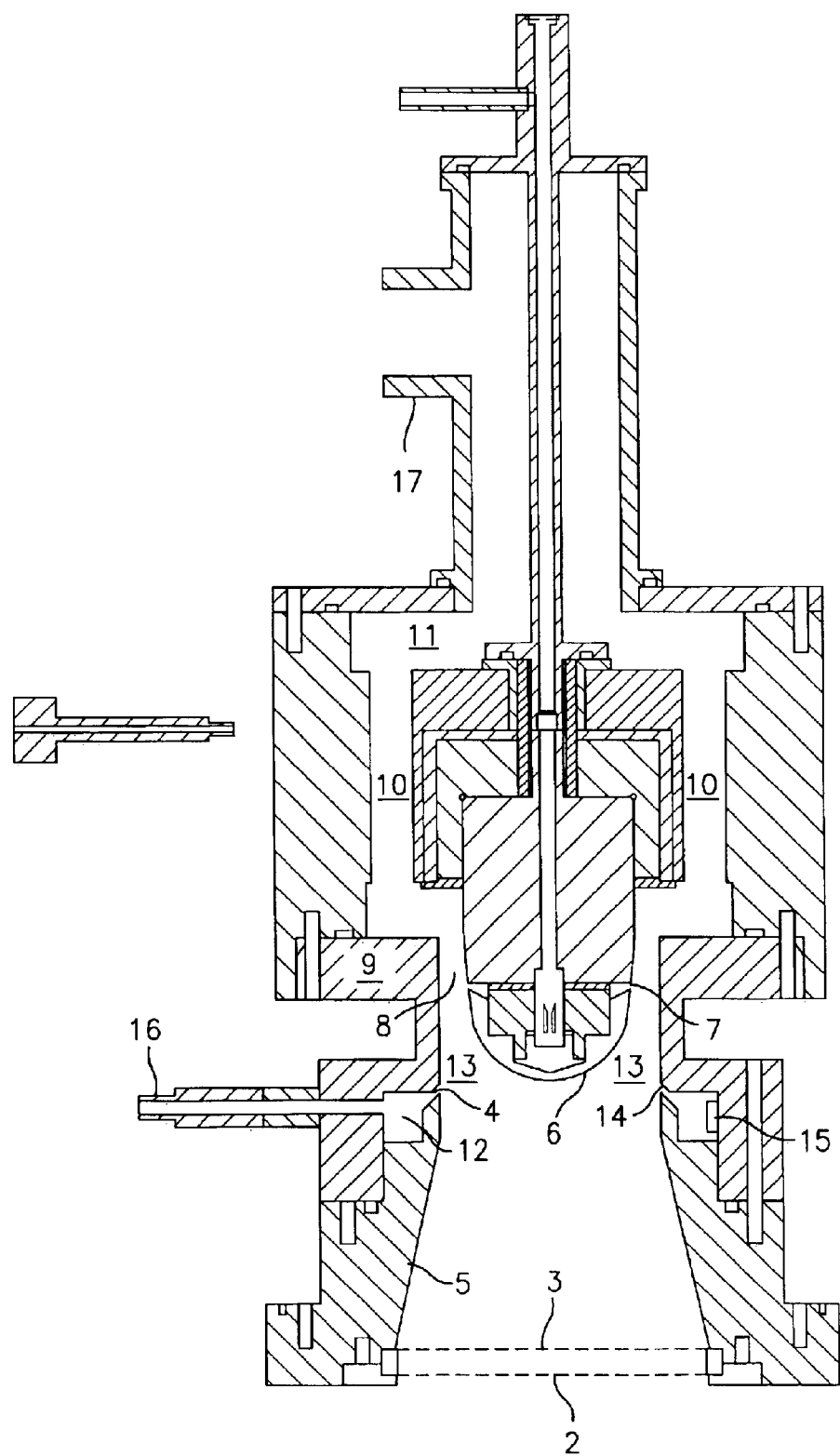
FIG. 1 is a view of a low resistance differential mobility analyzer gas exhaust constructed in accordance with a first embodiment of the present invention.
Figure 2:
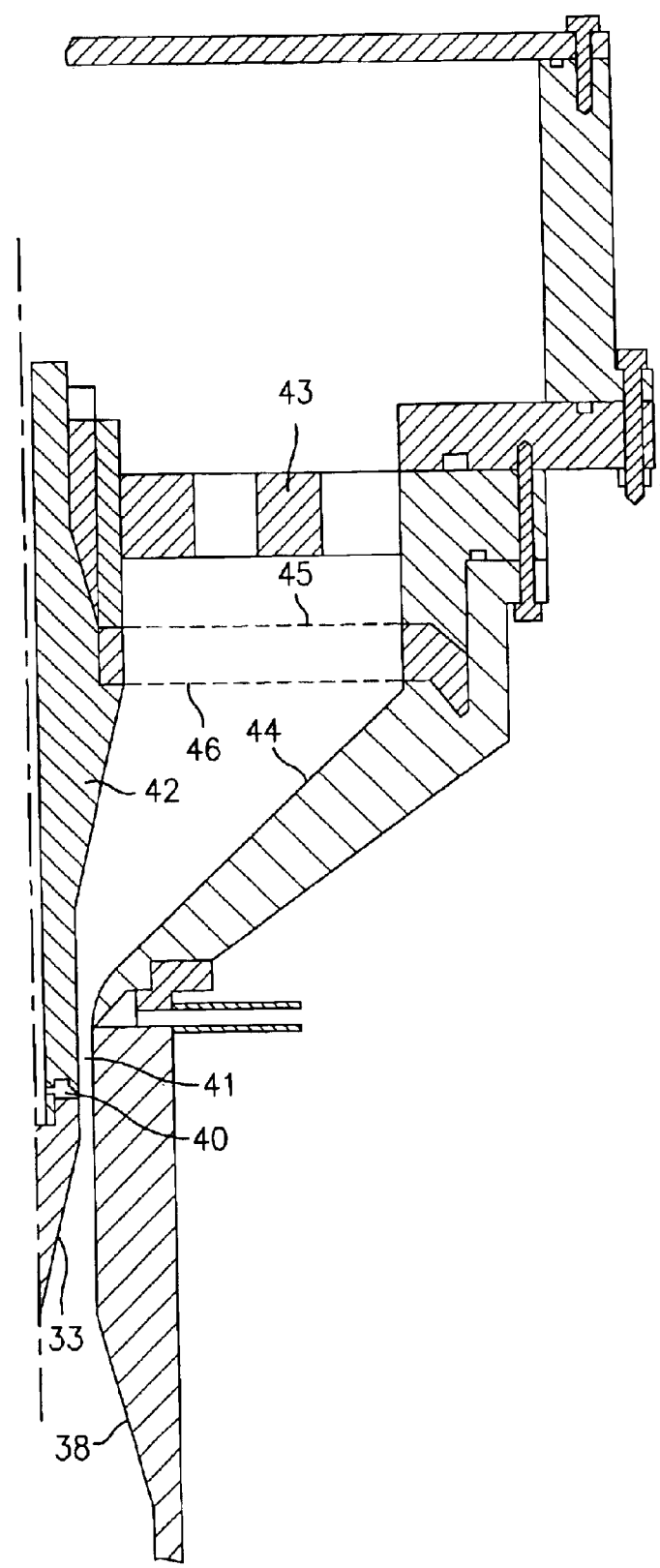
FIG. 2 is a view of a low resistance differential mobility analyzer gas exhaust constructed in accordance with a second embodiment of the present invention.

The various attributes of the present invention can be readily understood with reference to FIGS. 1 and 2.

FIG. 1 describes a differential mobility analyzer of the instant invention for separating particles or ions suspended in a gas, comprising: an analyzing region (13) in which ions are injected through slit (4) into a flow of ion-free sheath gas. This flow is introduced in (1) and is made highly laminar by passage through several screens (2, 3) of high uniformity, and then by acceleration through a converging section (5). The ions are injected into the analyzing section (13) from an inlet chamber (12) whose cross section and slit width (4) are designed so as to provide a relatively uniform ion stream along the length of the slit. The ions may be introduced from the outside through port (16) into the inlet chamber (12), or may be produced there by means of a charging device from volatile species ingested through port (16). Such a charger is incorporated in FIG. 1 in the form of a strip of $^{63}$Ni (15). At least two electrodes or grids (14 and 6) spaced apart from each other and charged to different voltages create an electric field in the analyzing region (13), which displaces the ions injected in (4) accross streamlines, and directs those having certain desired electrical mobilities into one or several collecting or sampling devices, such as the sampling slit (7).

The apparatus further comprises a flow constriction leading to a nozzle (8). In the embodiment of FIG. 1 this nozzle (8) serves the purpose of isolating the working region (13) from other regions further downstream, in order to avoid or reduce perturbations on the axisimmetry of steadiness of the flow in the working region. This constriction (8) is nonetheless moderate in the present invention in order to minimize pressure drop through the apparatus, thereby enabling attaining relatively high velocities and Reynolds numbers. To further isolate the analyzing region (13) from the pump moving the sheath gas flow, a first exhaust chamber (9) is provided downstream from the throat (8), which is in turn connected by means of at least three symmetrically placed tubes (10) (only two are shown in FIG. 1, of the ten actually present in the prototype rendered) to a second exhaust chamber (11). The intent of such buffers between the working region (13) and the exhaust line (17) going to the pump is to avoid propagation upstream of the flow assymetries existing on the downstream end of the instrument, but to do so with a relatively small pressure drop. Loss of axisymmetry in the working region would be fatal to resolution. Prior art has made use of only one sheath gas exhaust port. To avoid flow asymmetry potentially associated to higher gas speeds on the side of the instrument where this port is placed, a high pressure drop needs to be created in such designs between the position of the sampling slit (7) and the sheath gas exhaust port (17). The new multiport design of FIG. 1 greatly reduces the angular variations of gas pressure in the sheath gas exhaust chamber, allowing a comparable reduction in the required flow resistance. A secondary exhaust chamber (11) acts as a manifold that collects the various streams from the primary exhaust chamber into a single final exhaust port (17). The dimensions of the second exhaust chamber (11) are also such that the angular variations of pressure are small compared to the already small pressure drop along each of the ten exhaust lines.

FIG. 2 describes a second alternate embodiment of the instant invention, where the exhaust system is completely axysimmetric and no constriction is introduced upstream of the diffuser (33, 38). A slowly diverging diffuser following the sampling slit (40) enables substantial pressure recovery. This diffuser (33, 38) is essential in order to approach sonic conditions at the throat with high efficiency household vacuum cleaner motors, whose maximum pressure rise is generally well below ½ of an atmosphere, even in tightly encased two-stage systems. The apparatus differs principally from that described in FIG. 1 in the need to suspend the central electrode (42) from upstream, rather than downstream of the working section. Its support is a perforated piece (43), which also supports the outer elements of the DMA, including the laminarizing trumpet (44) and the laminarization screens (45, 46).

In the embodiment shown in FIG. 2, flow diffusion is achieved by introducing divergence not only in the final region of the inner electrode (33) but also at the end region of the outer electrode (38). But divergence in only one electrode would often suffice. One must note that the conventional criterion allowing diffuser semi-angles up to 3.5 degrees may not necessarily be appropriate under present conditions, as the inlet flow differs from the standard designs in being initially laminar rather than turbulent, which makes the flow far more prone to separate from the walls, reducing drastically diffuser efficiency. Thanks to the upstream support of the inner electrode, the exhaust line is completely axysimmetric and can be integrated directly to a high flow pump such as those commercialized by AMETEK (lamb electric division) for household or industrial central vacuum systems. Most desirable for the purpose is a clean pump where the gas is compressed without being passed through the motor region where it would be contaminated by dust. Also preferred are fully encased pumps whose exhaust gas is collected into a single outlet duct, which enables it being recirculated back into the shath gas inlet of the DMA (perhaps through a drying and filtering system if necessary). Notice also in the design of FIG. 2 that the supporting structure for the inner electrode is upstream the laminarization screens, in a relatively wide region where speeds are small, even in the perforated portion (44) of the main support piece (43). The pressure drop is therefore considerably smaller than in the design of FIG. 1. Furthermore, the slight loss of axisymmetry induced by passage of the flow through perforated support (44) is removed by the subsequent passage through the laminarization screens (46 and 45).

A slightly converging electrode geometry delays boundary layer transition to Re well above $10^6$, even in the presence of free stream turbulence levels of one or a few percent. Such levels can be attained with a moderately small inlet trumpet, such as that employed in the Vienna DMA, and do not require use of the large trumpet inlet proposed in U.S. Pat. No. 5,869,831. Although large inlet trumpets have the desirable advantage of reducing free stream turbulence, they are by far the bulkiest, heaviest and most expensive component of the DMA. It is therefore wise to avoid their use whenever such high degrees of laminarization are not absolutely essential to assure proper DMA performance. Free stream turbulence levels of 1% are certainly compatible with the attainment of resolutions of the order of 100, better than the current world record (close to 70) reached with a DMA provided with a large trumpet inlet but no converging working section.

One embodiment of the proposed converging DMA concept is shown in FIG. 1 for the case of an axisymmetric DMA. They combine particle-free fluid flow (the sheath gas introduced through (1)) and electric fields to drive charged particles introduced through a first narrow slit (the inlet or injection slit (4)) located in a first electrode or grid (14) into a second narrow slit or collector device (the outlet or sampling slit (7)) located in a second electrode or grid (6). The space between these two slits and electrodes will be referred to as the "working section" of the DMA. A particle-free sheath gas is introduced into a fluid flow inlet (1). Ideally, among the particles introduced through the injection slit, only those with mobilities contained within a relatively small range $\Delta Z$ centered about a mean value Z are sampled through the outlet slit. The inverse of the ratio $\Delta Z/Z$ is a measure of the DMA resolution.

Similar considerations do apply for non-axisymmetric geometries. To avoid boundary layer growth even upstream of the working section, the outer electrode or grid (5) in FIG. 1 is converging down to the inlet slit (4). Hoppel, The Ions in the Troposphere: their Interactions with Aerosols and the Geoelectric field, Ph.D Dissertation, Catholic University of America (1968) and Hoppel, Measurement of the Mobility Distribution of Tropospheric Ions, Pure and Applied Geophysics, Vol. 81, pp. 230–245 (1970), (1968, 1970), designed and built a planar wedge-shaped aspiration counter with straight converging walls. Hoppel described some key advantages associated to his convergent geometry. However, he did not reach Reynolds numbers in the high range of interest here, and his work did not demonstrate a resolution anywhere near the values sought here and required for chemical and biological analysis. Furthermore, aspiration counters differ in many ways from DMAs, since the full flow rather than a small part of it carries charged particles This makes it undesirable to use a large laminarization chamber with inlet filters and screens, so that convergence in the working region is more necessary than in DMAs. Aspiration counters do not have either an injection slit, so that the stabilization requirements in these instruments are considerably milder than in DMAs.

Unusually large acceleration at the injection slit or downstream from it, stabilizes the associated mixing layer, even at the very large Reynolds numbers of interest here. This goal is achieved partly as in the Vienna DMA by a slight convergence of the outer electrode (5) immediately following the inlet slit (4) (FIG. 1). But considerably higher convergence may sometimes be desirable. One extreme embodiment of the present invention's high stabilization of the mixing layer at the inlet slit is shown in FIG. 1, where the leading edge of the bullet-shaped inner electrode is located in the immediate vicinity of the inlet slit section. Prior art has placed this bullet top far upstream of the inlet slit. There it serves the useful purpose of accelerating the flow and hence reducing the relative importance of free-stream, turbulence. However, it does not help stabilize the mixing layer, which is the most fluid-dynamically unstable region of the whole flow field. Aside from its stabilization advantage, the lowering of the bullet forces a departure from the strong tendency of prior art to use nearly parallel plate or cylindrical geometries, where the theoretical response function of the DMA is easily calculated and no calibration is needed to infer particle or ion mobility. The advantage of a calibration-free instrument is sacrificed in the present invention in favor of the preferred goal of increasing resolution. The need for calibration is inevitable here in view of the fact that the whole geometry needs to be convergent. However, precise mobility standards for calibration have recently become available in the nanometer range, so that the traditional reasons for favoring non-converging geometries no longer apply.

Figure 3:
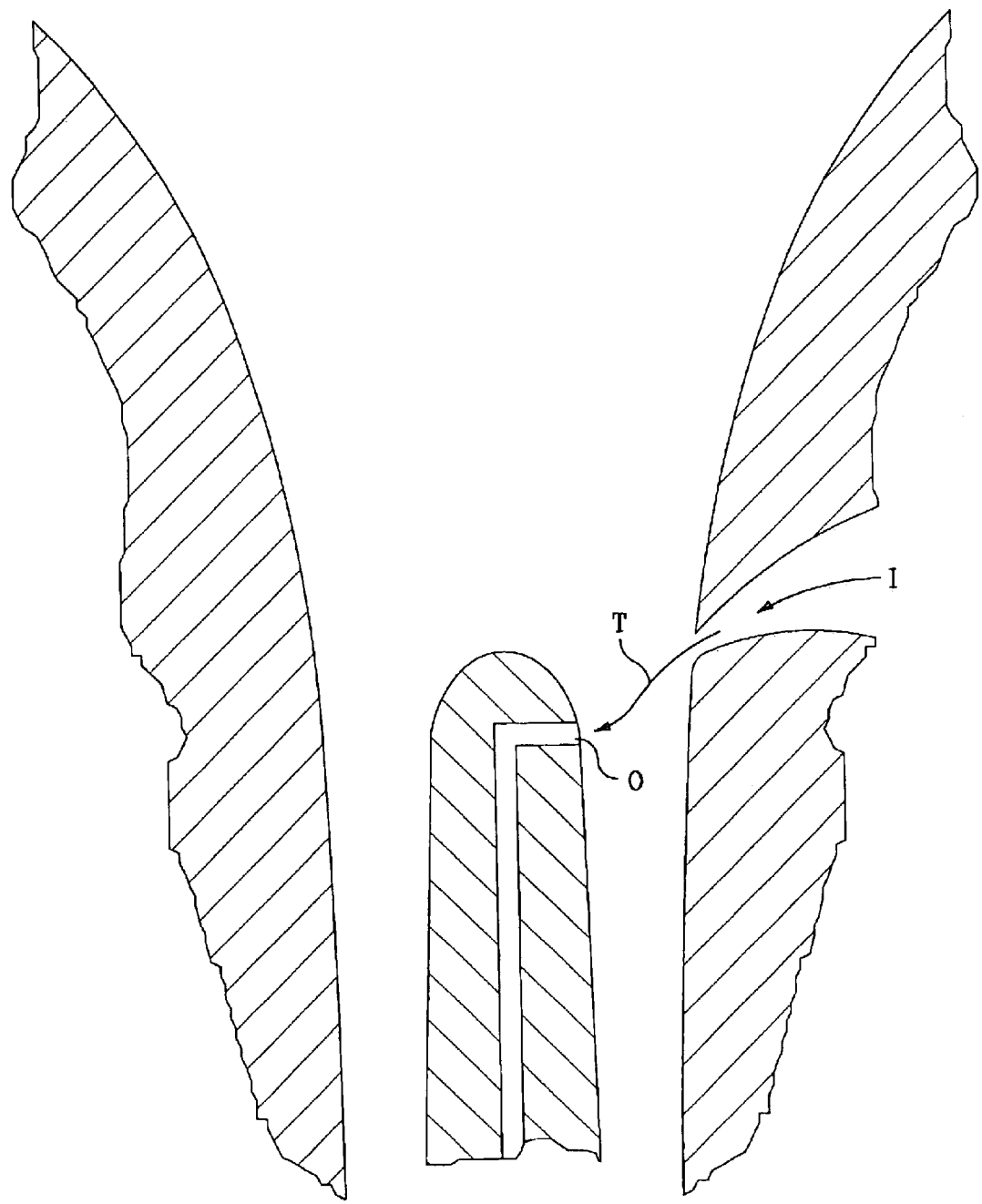
FIG. 3 is a view of a geometry for a two-dimensional fluid flow through the differential mobility analyzer.

De la Mora (2002) demonstrated theoretically that the quantity H related to DMA resolution is unity under the best of circumstances considered, and larger than unity in all other cases studied, and refers without detail to different unpublished geometries discovered by Dr. Michael Labowsky (Wayne, N.J.), for which H can be smaller than unity, and which are therefore superior to those previously known. One example of such special geometries is provided in FIG. 3 for two-dimensional flows, where the central element is at ground and the two elements surrounding it are at the same voltage. Inlet and outlet slits are indicated (I and O) as well as an ion trajectory (T) going through both slits. Labowsky's design differs from the geometries considered in de la Mora (2002) in that the boundary conditions for the stream function and the electrical potential do no longer coincide with each other at the plane of symmetry. The same feature arises in axisymmetric flows in geometries where the inner electrode is bullet-shaped, such in the DMA of Rosell et al. However, for this feature to yield H values below unity certain special precautions are necessary. One possible approach is to lower the bullet nose from its traditional position (well above the inlet slit) into a region closer to the inlet slit, or downstream from it, where its electric field is felt by the ions as they emerge through the inlet slit. The axisymmetric analog of FIG. 3 provides another example where the same advantage arises. Again, the advantage requires certain unusual features, such as the proximity characteristic mentioned, which are not met by any axisymmetric or two-dimensional DMA built to date.

We note that the extreme acceleration shown in FIG. 1 in the vicinity of the inlet slit (4) may not be necessary in many cases where a more slowly converging geometry would assure the stability of the mixing layer following the aerosol inlet. In such cases it is in fact preferable to moderate the abruptness of the convergence for several reasons. First, the flow field will be more uniform, which in turn favors overall stability. Second, de la Mora (2002) has shown that excessive acceleration often leads to a loss of resolution with respect to the value given in equation (1) for the case of a cylindrical design. Third, earlier acceleration would reduce earlier on the level of free stream turbulence, which would hence be smaller if the ojive of the electrode (6) were to be placed further upstream than shown in the embodiment of FIG. 1.

An alternative embodiment of the present invention accelerates the flow by a combination of various degrees of convergence on the outer and inner electrodes. In addition to the stabilization advantages just described, we note the fact that U.S. Pat. Nos. 5,869,831 and 5,936,242 protect DMAs with a laminarization system delivering a laminar flow at Reynolds numbers above 2000 into the working section inlet. By introducing acceleration in the working section, the present invention covers situations where the laminarizing means provides laminar flows below 2000 to the inlet of the working section, but subsequent acceleration within the working section may increase considerably the Reynolds number in downstream regions of the working section. As discussed in de la Mora (2002), considerable acceleration (hence increase in Re) can be achieved in axisymmetric geometries with acceptable resolution loss. Since the resulting resolution is primarily determined in the final portion of the working section (where Re is highest in such accelerating designs), it is possible without making use of the abovementioned U.S. patents to attain resolving powers much larger than in nonconverging DMAs running at Re<2000.

A design including low-resistance sheath gas exhaust greatly reducing the pressure drop through the instrument, enables attainment of gas velocities well in excess of 100 m/s with relatively light and inexpensive pumps, such as those used in high efficiency household vacuum cleaners and central vacuum cleaners.

Another embodiment of the present invention comprises a method to achieve better laminarization conditions at the beginning of the working section than previously obtained, even with a large inlet trumpet. This new method uses a small inlet trumpet, such as that in the Vienna or the Rosell DMAs. At sufficiently large sheath gas flow rates, the flow passing the inlet screen becomes turbulent. This turbulence survives for a certain distance downstream, which appears as undesirable from the viewpoint of achieving a highly laminar flow. On the other hand, this turbulence provides excellent mixing, and the flow becomes highly uniform on the average. Hence, provided that this flow returns to a laminar state before it reaches the inlet slit, the introduction of turbulence in the screen is desirable rather than undesirable as it yields a highly uniform as well as a highly laminar flow. The present improvement therefore involves (a) choosing a screen cross-section, transparency, and wire diameter such that (at a given gas flow rate) the flow through the screen becomes turbulent. The criterion for this to happen is well known to fluid dynamicists, and involves a Reynolds number about the screen wire larger than about 40, (based on local speed and wire diameter), when the Karman vortex street sets in; (b) Using a moderately converging geometry following the screens, such that, if the flow were laminar, it would remain laminar, while a turbulent flow would tend to relaminarize; and (c) Choosing a sufficiently long distance between the screen and the aerosol inlet slit, and making the screen wires and opening sufficiently small for the turbulent flow to actually relaminarize before it reaches the aerosol inlet slit. Note that relaminarization at high flow Re in the channel requires a convergent wall, such as discussed in de la Mora (2002). But, as discussed, it does not require a high convergence angle, so that a relatively modest convergence ratio (such as that in the Reischl or the Rosell DMA) provides a relatively long path for relaminarization. Hence, it is preferable to use small convergence angles (yet large enough to assure flow stability as discussed in de la Mora (2002)) because this provides a greater downstream distance for relaminarization. The required relaminarization distance is well known to fluid dynamicists familiar with the field of grid turbulence. It can be accommodated in moderately sized designs by making the screen wire and opening sufficiently small, and making the distance between the screen and the inlet slit sufficiently long. For example, a screen transparency of 27% with screen wire diameter of one or a few thousands of an inch followed by a conical section with a half angle of 10 degrees enables substantial relaminarization considerably before the flow cross section is reduced to ⅕ of its initial value. For this scheme to function successfully, it is not essential that the flow becomes turbulent past the screen, provided that the screen is highly uniform, as many commercially available screens actually are. Hence, earlier art based on large inlet screens where the flow does not become turbulent is also suitable to produce a uniform laminar flow. However, there is an advantage in attaining this laminar state with a small trumpet, as the manufacturing cost and weight of the instrument can be drastically reduced.

A disadvantage of the small over the large inlet trumpet is that a small screen area with a small screen transparency tends to produce high pressure drop, and hence yields a smaller flow rate with a given pump. The present invention includes a means to counteract this problem without making use of previous art based on large laminarization trumpets. The new procedure uses first a wide flow cross-section with one or several filters, and one first screen of low transparency (say 30%). The flow resistance is small in spite of the low transparency because the area is large. Then follows a convergent region, and finally the true laminarization screen with small cross section, as described in point 3. The difference with 3 is that this laminarization screen may have a large transparency and hence a low pressure drop, without loss of the advantages described in point 3. In other words, prior art used first a low transparency screen and a high transparency screen for laminarization, both in a large cross sectional area, followed by a convergent region. This arrangement is typical of wind tunnel inlet designs, and is widely used in fluid mechanical laboratories. The president invention uses a high cross-sectional area only for the upstream filters (if any) and the low transparency screens, and introduces the high transparency screen somewhere within the convergence region. It includes all the advantages described above without the disadvantage of the high pressure drop.

Another preferred embodiment of the present invention is such that the maximum displacement of the axis of one cylinder from the axis of the other is less than one thousandth of an inch, preferably less than half a thousandth of an inch.

Knutson, The Distribution of Electric Charge Among the Particles of an Artificially Charged Aerosol, Ph.D. Thesis, University of Minnesota (1971) considers the effect that a parallel displacement $\epsilon$ of the axis of one of the cylindrical electrodes with respect to the axis of the other cylinder has on DMA resolution. His numerical results for the particular case of the DMA disclosed in Knutson et al., Aerosol Classification by Electrical Mobility: Apparatus, Theory and Applications, J. Aerosol Sci., Vol. 6, pp. 443–451 (1975) show that the full width of the resulting distribution broadening $\Delta Z/Z$ would be close to $4\epsilon/(R_2-/R_1)$:

$$\Delta Z/Z=4\epsilon(R_2-R_1)+O(\epsilon^2). \quad (5)$$

Our analysis in the limit of small eccentricity E shows that this result is almost independent on the ratio of radii when $R_1/R_2>0.5$.

Both results hold only in the absence of other broadening mechanisms such as diffusion. We also find that the instrument's response function f(Z) has turning points at its edges $Z=Z_0\pm\Delta Z/2$. This makes it singular, so that the more commonly used measure of $\Delta Z$ based on the full distribution width at half height (FWHH) is also equal to $4\epsilon/(R_2-R_1)$. The goal of attaining FWHH values as small as 1% hence requires $\epsilon<0.01\Delta/4$. For $\Delta=0.5$ cm, $\epsilon$ must be smaller than 12.5 $\mu$m (0.419 thousands of an inch). Such tolerances are considerably more demanding than those previously attained in commercial DMAs, but are most desirable for the objectives of the present invention.

Consider now a situation where the eccentricity is 0.0005 inch. When the DMA is mounted on a lathe centered with respect to one of the electrodes and an indicator is placed on the other electrode, the maximum displacement of the indicator will then be 0.001 inch. This value is typical of a good machining job, since at least half that clearance between critical parts is necessary for them to fit into and out of each other, unless special surface treatments such as grinding or honing are applied (however, much better centering can be obtained with conical rather than cylindrical fittings). The DMA of FIG. 1 has three such critical fittings. $\Delta Z/Z<1\%$, then $\epsilon R_2(R_2-R_1)$ must be smaller than 0.25%. When $\epsilon R_2<0.0005''$, this requirement can be reached provided that $R_2-R_1>5$ mm, but is more easily met in a DMA with twice that gap. Such tolerances are considerably more demanding than those previously attained in commercial DMAs, but are most desirable for the objectives of the present invention. These results hold only in the absence of other broadening mechanisms such as diffusion.

The previous calculation is based on the assumption that the velocity field is either flat or fully developed. However, the presence of eccentricity would tend to create an angular dependence of the width of the throat region. According to Bernouilli's law, the gas speed at the throat would be angularly uniform. But if the gap is not uniform, the local flow rate per unit length Q would also vary along the slit length. The flow speed in the working section would then be smaller in the regions with a narrower gap, where the radial field is larger and the radial distance to travel is smaller. This additional effect is likely to turn FWHH into $6\epsilon/(R_2-R_1)$ instead of the more conservative $4\epsilon/(R_2-R_1)$ given in equation (5). Although such conclusions are drawn for the case of a plane or cylindrical geometry, they apply with slight corrections to the case of slowly converging geometries such as that of FIG. 1. They hold also approximately in more rapidly converging geometries.

The DMA of Knutson et al. (1975) provides for an axisymmetric injection of the aerosol flow through the inlet slit. This design, however, is associated to large losses of particles smaller than 5 nanometers by diffusion to the aerosol inlet walls. This problem is partly overcome by the split-flow design in the nanoDMA of Chen et al., Design and Numerical Modeling, presented at the AAAR Annual Meeting, Orlando, Fla., October 14–18 (1996), and Chen et al., Numerical Modeling of the Performance of DMAs for Nanometer Aerosol Measurement, J. Aerosol Sci., Vol. 28, pp. 985–1004 (1997). However, this design has not yet demonstrated an ability to transmit and size particles with diameters smaller than 3 nanometers. In contrast, the Vienna DMA introduces the aerosol stream through a short lateral tube into an aerosol inlet chamber immediately preceding the inlet slit. Losses of very small particles are thereby greatly reduced with respect to truly axisymmetric designs, with a demonstrated ability to transmit even small ions. This improvement, however, comes at a cost. As represented in FIG. 1, the inlet chamber (12) is annular or straight for cylindrical or two-dimensional DMAs, respectively, both cut on one side by the slit (4). The flow of aerosol through the slit into the working chamber is driven by the difference in pressure of the gas upstream and downstream the slit. But since the aerosol stream has to travel from the inlet tube along this inlet chamber to reach all points of the slit, and this travel requires a certain pressure drop, the aerosol tends to reach the working region of the Vienna DMA predominantly through the portion of the slit facing directly the aerosol entry tube. Swirl may perhaps reduce this problem, but does not eliminate it. Two main problems follow from this asymmetry. First, since the peak width $\Delta Z$ increases linearly with the local ratio of the aerosol to sheath gas flow rates, it is larger than the average at some points, which reduces the resolution of the instrument. Second, the shear layer instability that tends to arise following the injection slit can be moderated by suitable choice of the ratio of mean speeds between the aerosol and the sheath gas. This control, however, becomes harder when the aerosol flow is not uniform along the slit length.

The aerosol injection chamber is designed in the present invention such that the pressure drop along the perimeter of the chamber is much smaller than the pressure drop across the slit. This goal is achieved by making the cross section of the chamber sufficiently large and the injection slit channel sufficiently narrow and long.

The correct selection of the width $\delta_i$ of the aerosol inlet slit is of considerable importance, and an improper choice can lead to poor resolution for a variety of reasons. At first glance it would appear that $\delta_i$ must be relatively narrow at the scale of the axial distance L between the two slits, or else the initial spatial spread of the aerosol flow would reduce resolution. However, the electric field accelerates radially the entering aerosol and immediately makes its axial cross section relatively independent of $\delta_i$. Consequently, this first criterion leaves $\delta_i$ free. A second criterion putting bounds on $\delta_i$, is that it should not be so small as to form a wall jet moving faster than the sheath gas, since this would tend to destabilize further the mixing layer. Under operating conditions leading to high resolution ($q_a/Q<0.01$), and using a ratio $\delta_i/L$ larger than 0.01, this requirement is almost always met. Hence, although the aerosol speed will generally be smaller than the sheath gas speed, the intense acceleration imposed in this region still assures stability. Under certain conditions, such as for instance, when analyzing particles past the upper size range of the instrument, it may be necessary to reduce Q below 100 or even 30 liters/minute, which is likely to force use of $q_a/Q$ ratios well above 1%. For such cases, it is essential to increase $\delta_i$ so that the aerosol ejection speed does not exceed too drastically the mean sheath gas speed. The slit width of the DMA shown in FIG. 1 can be changed by inserting shimstock pieces at the union of the two pieces defining the slit. Another consideration suggesting the use of larger rather than smaller inlet slit widths is the fact that diffusion losses increase as $1/\delta_i$. The variable slit design of this instrument therefore allows its widening in cases when the signal is too small, and a reduction of transmission losses carries more weight than other considerations.

Accordingly, the ideal range in this invention for the vertical elevation of the inlet slit top over its bottom is between $0.025\Delta$ and $0.1\Delta$, with a preferred value of $0.05\Delta$. The dimensions of the aerosol chamber preceding the inlet slit in the cylindrical DMA of FIG. 1 have been determined such as to meet the requirements of the previous paragraph using the preferred elevation of $0.05\Delta$. An excessive chamber cross section is undesirable because it would promote the loss of small charged particles by space charge.

A serious difficulty associated to axisymmetric DMAs is the relatively high loss of nanometer particles through its inlet up to the point past the aerosol injection slit. Such losses are particularly high in the case of intense sources of unipolarly charged particles, such as electrosprays. A solution to this problem was proposed in U.S. Pat. No. 5,869,831 involving a planar DMA configuration with two orifices rather than two slits. That principle can be used similarly in the case of DMAs with converging walls, and is thereby incorporated into the present invention, either for mass spectrometric applications or for other purposes.

Axisymmetric DMAs may therefore not be the most competitive instrument in dealing with certain analytical applications with intense unipolar ion sources at atmospheric pressure. However, in situations such as monitoring of explosives or drugs, where the volatile species to be detected are initially neutral, there would be no loss of analyte at the inlet of the DMA. In other cases where a neutral analyte is volatile at temperatures higher than that at the DMA inlet line, losses by diffusion may still exist, but the generally stronger losses associated to space charge would still be absent.

In such situations and in many others, an axisymmetric DMA geometry such as that shown in FIG. 1 offers advantages over the two orifices placed in two parallel or converging walls just discussed in relation to U.S. Pat. No. 5,869,831. The reason is that, at sheath air flow rates of 3000 liters/minute, the aerosol flow could, without loss of resolution, be as high as 30–60 liters/minute. This flow rate is vast compared to the throughput that can be passed through a typical atmospheric pressure inlet to a mass spectrometer, and would be ideally suited for situations involving highly dilute and difficult to detect analytes. In such cases, the species to be detected would be charged in the aerosol inlet chamber, immediately upstream of the injection slit, thereby minimizing the loss of analyte ions by diffusion to the walls once they are formed. A variety of schemes can be used for the purpose of charging the analyte vapor molecules, including a radioactive source placed through the whole or a portion of the perimeter of the aerosol inlet chamber (for instance, a ring or d washer of $^{63}$Ni, $^{210}$Po, or another alpha or beta emitter). In this case, some of the considerations made earlier regarding the dimensions of the aerosol inlet chamber would have to be modified in order to assure a suitable charging efficiency, though those familiar with the problem of charging of small ions and ultra fine particles in such environments can readily design such a chamber. Note that an inlet chamber larger than that of FIG. 1 will often be required, but will not increase unreasonably the losses of ions under the present in-situ charging conditions. Therefore, this invention also includes variously converging axisymmetric DMAs with a radioactive source spread over all or part of its aerosol inlet chamber. We note that charging schemes other than those relying on radioactive sources are also included within the scope of this invention. In fact, *Ion Mobility Spectrometry*, by Eiceman et al. (CRC Press, FL, 1994) discusses the complexity of the ion types produced by radioactive sources, and the need for using highly purified gases that may not be easily provided at the rates required for the sheath flow in a DMA. Cleaner ion sources such as, for instance, those developed by F. Eisele and colleagues Ref would therefore be even more useful for the analysis of volatiles in DMAs.

Another objective of this invention is to identify conditions enabling the construction of DMAs enjoying both wide size range and high resolution operation.

The short DMA of Rosell et al. (1996) has a length L approximately twice the optimal value L*, and achieves as a result a resolution in the nanometer range substantially higher than the similar but much longer Vienna DMA, where L/L* is close to 15. However, the gains in resolution obtained for very small particles in the short DMA come at the cost of loss of the ability to analyze larger particles characteristic of the long DMA. This is a direct result of the fact that, all other things being equal, the mobility of the particles selected by the DMA varies inversely with its length L:

$$Z^{-1} = 2\pi L V \ln(R_2/R_1)/Q, \tag{6}$$

where V is the voltage difference applied between the two electrodes.

A general problem with all the DMAs discussed so far in the literature, including those commercially available from TSI and Hauke (Vienna model) as well, as short experimental models is that, if they work well with very small particles, they tend to have a limited range with larger particles, or if they can cover the range of large particles, they tend to have a poor resolution with very small particles. Since manufacturers of long or medium size DMA often make the claim that their instruments are suitable for the analysis of particles as small as one or a few nanometers, while those of medium size DMAs sometimes do also claim an ability to analyze particles as large as 100 nanometers, we will subsequently define the proper range of an instrument in terms of the maximum and minimum mobilities $Z_{max}$ and $Z_{min}$ which they can analyze with a resolution higher than a certain minimum. Without that minimum resolution constraint, it is clear that there is no upper or lower limit for Z, since either the voltage V or the flow rate can in principle be reduced to arbitrarily small values. Considering the substantial number of DMAs built to date, it would seem that the hope of designing one DMA able to deal simultaneously with small as well as large particles is futile. The notion that analyzing particles 50 or 100 nanometers in diameter calls for relatively long DMAs, while particles a few nanometers in diameter require short DMAs are both well established in this field. These impressions are in fact readily proven to be inescapable in the case of two-dimensional or narrow gap cylindrical DMAs ($R_2/R_1 - 1 = \Delta/R_1 \ll 1$), when (6a) reads $$Z = \frac{Q}{2\pi R_1} \frac{\Delta}{LV}; \text{ when } R_2/R_1 - 1 = \Delta/R_1 \ll 1. \tag{6b}$$

The group $Q/(2\pi R_1)$ is just Q', the flow rate per unit length characteristic of the two-dimensional geometry, so that $ZV/Q' = \Delta/L$. Since the quantities V and Q are limited to a certain finite range, it is clear that long DMAs with larger values of L/Δ favor small particles, and short DMAs have the opposite property.

Such a situation is unproblematic for a number of applications. For instance, the identification of drugs and explosives by mobility analysis requires instruments capable of dealing only with particles smaller than 3 nanometers, for which a short DMA suffices. Most traditional DMA applications deal with particles larger than 5 nanometers, for which the long Vienna design is more than adequate. However, there are other applications where high resolution in the 2–5 nanometers range is as essential as the ability to analyze particles as large as 30 nanometers. One example is in monitoring industrial polymers, where (he molecular weights of interest span the range from several thousand amu (2–3 nanometers) to several million amu (15–30 nanometers). In this case, the powerful and widely used technique of electrospray mass spectrometry fails to offer a satisfactory analytical solution due to peak congestion associated to the presence of many masses, each in numerous different charge states.

(MALDI) Matrix assisted laser desorbtion ionization mass spectrometry is in principle less prone to peak congestion since it tends to produce mainly singly charged ions. But the ionization process is strongly dependent on polymer mass as well as the chemical nature of the analyte and the matrix, which makes problematic the quantitation of polymer mass distributions over their typically broad mass ranges. The masses in the related problem of protein or nucleic acid analysis range similarly from several thousand amu, up to several millions. This situation is often, but not always, amenable to electrospray mass spectrometric investigation, and would also benefit from the availability of alternative fast and inexpensive techniques such as that provided by DMAs. Since DMAs have a much higher mass range than mass spectrometers, the procedure of reducing to unity the charge of electrospray ions is still compatible with their mobility classification at mass to charge values even beyond $10^7$ amu. In these important two examples just mentioned, and probably in many others, it would be very useful to develop a DMA capable of covering at high resolution the whole size range, from at least 2 nanometers up to 30 nanometers.

Equation (6) shows that, for a given cylindrical DMA geometry (given $R_1$, $R_2$ and L), the smallest value of Z attainable (lowest mobility range) corresponds to the largest voltage and the smallest flow rate. Brownian motion is generally relatively weak in the small mobility region, so that the main factor limiting resolution (in mechanically and fluid dynamically well designed instruments) is the ratio $q_a/Q$ of aerosol to sheath air flows. Resolution is highest when the aerosol inlet flow is close to the aerosol outlet flow, and we will consider only this most favorable situation, where FWHH is equal to $q_a/Q$. The resolution criterion that FWHH be smaller than 1% therefore fixes this flow rate ratio to be smaller than 1%. Clearly, less stringent resolution standards would allow smaller flow rate ratios. In principle, the constraint $q_a/Q<0.01$ places no direct limits on Q. In practice, however, most existing detectors for nanoparticles and ions use aerosol flow rates $q_a$ of the order of 1 liter/minute. Losses in the transmission lines tend to be substantial at lower flow rates, and serious detection difficulties tend to appear. We will therefore base the following estimate on a minimum acceptable aerosol flow rate of 1 liter/minute, and a corresponding $Q_{min}=100$ liters/minute. Much smaller Q values are commonly used in DMAs, but they are invariably associated to resolutions much smaller than set here. The next consideration is how large V can be. The limit is imposed by the appearance of electrical discharges. This limit is generally weakly dependent on the ratio $R_2/R_1$, and essentially independent on L. Therefore, a value of $10^4$ volt, typical of commercial DMAs, will be adopted. With the choices $V_{max}=10^4$ volt and $Q_{min}=100$ liters/minute we find $Z_{min}=C/(L\ln(R_2R_1))$, which in terms of the variables $L^*$ and b of equations (2–3) may be written:

$$Z_{min}=C/(bL^*\ln(R_2/R_1));\ C=0.2652\ cm^3/s. \tag{7a,b}$$

In order to offset the strong peak broadening effects in the highest mobility range, DMAs must operate at large sheath air flow rates. Hence, the ratio $q_a/Q$ is typically smaller than 1%, and the resolution of a well designed DMA is well described by equation (1). The condition $\Delta Z/Z<1\%$ then implies that $D/(L^*U)$ $(b+1/b)<1.85\times10^{-5}$. Expressing D in terms of Z via (4) and using $Q=\pi(R_1^2-R_2^2)U$, we find $$Z_{max}=AL^*/(R_2^2-R_1^2)/(b+1/b); \tag{8a}$$

$$A=1.85\times10^{-5}eQ/(2\pi kT). \tag{8b}$$

In the case of particles or ions carrying z elementary charges, the constant A would be further multiplied by the charge state z. We will nonetheless base the discussion on the least favorable condition where z=1, since this situation simplifies the interpretation of a mobility spectrum as a size distribution. Evidently, the larger Q the higher the mobility that falls within the analyzable range. High efficiency household vacuum cleaners or central vacuum systems reach flow rates larger than 3000 liters/minute provided that the pressure drop is moderately small, as is the case of DMAs built according to the present invention. We will therefore base the present estimate on a value of $Q_{max}$ of 3500 liters/minute. Considerably larger values can be obtained by combining two or more such pumps in parallel. At room temperature, this yields $$A=6.7\ cm^3/s. \tag{9}$$

A most important quantity characterizing the instrument's range is the ratio $Z_{max}/Z_{min}$:

$$Z_{max}/Z_{min}=(A/C)F(R_1/R_2)/(1+1/b^2); \tag{10}$$

$$F(y)=\ln(1/y)(1-y^2)/(2+2y^2). \tag{11}$$

The group A/C takes the value 252 in the present estimate, but can be made considerably larger by relaxing the resolution requirement. The group $(1+b^{-2})^{-1}$ plays a limited role, because only the domain b>1 is of practical interest. In this region, $(1+b^{-2})^{-1}$ varies only from ½ (b=1) to 1 (b=∞). Even at b=2, at which the resolution is very close to the optimal value corresponding to b=1, the factor $(1+b^{-2})^{-1}$ differs only by 20% from unity. At b=3, $(1+b^{-2})^{-1}=0.9$. Once b>3, $(1+b^{-2})^{-1}$ approaches closely its large b asymptote where both $Z_{max}$ and $Z_{min}$ decrease linearly with L (or b), so that their ratio is independent of b. In contrast, the ratio $R_1/R_2$ has a very strong effect on the range through the function F, as illustrated in Table 1.

TABLE 1

| | | | | Function F defined in Equation 11 | | | | | |
|---|---|---|---|---|---|---|---|---|---|
| F(y) | 0.5 | 0.487 | 0.452 | 0.4328 | 0.413 | 0.395 | 0.347 | 0.28 | .252 | .213 |
| y | 1 | 0.757 | 0.56 | 0.5 | 0.444 | 0.4 | 0.3 | 0.2 | 0.15 | 0.1 |

The range function F(y) increases monotonically with y, and reaches its largest value $F_{max}=\frac{1}{2}$ in the vicinity of y=1 (2-D DMA limit). Although there is a considerable penalty against DMAs with wide gaps (where $R_2/R_1-1$ is not small), a ratio $R_1/R_2=0.56$ is still tolerable, with less than 10% loss of range with respect to the two-dimensional limit. Under the most favorable conditions when $R_1/R_2>0.56$ and $b>3$, the maximum ratio $Z_{max}/Z_{min}$ is A/(2C), affording only a range of mobilities slightly larger than two orders of magnitude:

$$Z_{max}/Z_{min} < A/(2C) = 126 \tag{10b}$$

The range of mobilities spanned by air-suspended particles with diameters going from 2 nanometers to 100 nanometers is considerably wider than 100, implying that it is not possible to cover it fully with a single instrument for the conditions of resolution, flow rates, voltages and temperature set here. The ratio A/C may be written as:

$$A/C = \frac{(\Delta Z/Z)^2}{8\ln 2} \frac{Q_{max}}{Q_{min}} \frac{eV_{max}}{kT} \tag{10c}$$

and is therefore not necessarily fixed as 252. For instance, sacrificing a factor of two in resolution ($\Delta Z/Z=2\%$) increases $Z_{max}$ by a factor $2^2$ (by allowing operation at smaller voltages) and decreases $Z_{min}$ by another factor of 2 (by allowing operation at smaller $Q_{min}$). The range therefore increases strongly with slight reductions in resolution. $Q_{max}$ can also be increased in principle well above the 3500 liters/minute set earlier. Given a large enough blower, it is in fact possible to build a DMA with rather small $Z_{min}$ while keeping b close to the optimal value. A narrow-gap design with the same $Z_{min}$ as the Vienna DMA ($6.45 \times 10^{-4}$ cm$^2$/V/s according to equation (7)) would require $bR_2=41$ cm, leading to an unusually wide instrument ($R_2=13.66$ cm for b=3).

A more practical approach to cover the full range of particle sizes from 2 nanometers up to 100 nanometers is to use two widely different lengths L by means of two interchangeable inner electrodes with sampling slits located at different positions. Therefore, one embodiment of the present invention capable of reaching high resolution over an unusually wide range of mobilities consists of a DMA where one of the electrodes is interchangeable, so that the variable b can take in one electrode configurations values in the vicinity of the optimal (1<b<4), and considerably larger values of the order of 10 in another electrode configuration. This method has been used by Rosell et al., (1993, 1996) in a DMA with the inner and outer diameters identical to those in the Vienna DMA. Their short bullet had L=1.6 cm (b=2.143), for which equations (8a) and (9) yield $Z_{max}=0.46$ cm$^2$/V/s (mobility diameter of 2 nanometers). Their long bullet had L=11.4 cm, for which equations (7a–b) yield $Z_{min}=6.5 \times 10^{-4}$ cm$^2$/V/s. The total range with this combination is $Z_{max}/Z_{min}=708$. The sheath air outlet of the DMA of Rosell et al. (1996) was also that of the Vienna design, had therefore a high pressure drop, and could evidently not reach flow rates as high as 3,500 liters/minute. This limitation is resolved in the low resistance outlet system of FIG. 1. In this case, the throat is much wider than in FIG. 2, the corresponding pressure drop is relatively small ($U_{max}=40$ m/s) and no diffuser is necessary.

Another embodiment of the present invention is an axisymmetric DMA of fixed geometry approaching conditions for maximum range, with a preferred geometry such that b is near 3 and $R_1/R_2>0.56$. A two-bullet DMA can also be implemented to widen the $Z_{min}$ range of an instrument such as that in FIG. 2, meant to cover the nanometer and subnanometer range. However, in this case, $Z_{max}$ is too large and $R_2/R_1$ too small, which precludes reaching values of $Z_{min}$ as small as in the Vienna DMA except with unduly large b values (b=71 for a DMA with $R_1=4$ mm, $R_2=9$ mm). This design is therefore ideal for applications such as drug and explosive analysis requiring high resolution at high mobilities, but not so for applications requiring the widest possible range. Other special applications such as protein and polymer analysis can be handled with a single-bullet design by shifting the DMA radii to values larger than in FIG. 2, while approaching the high asymptote of the range function F(y) by using a ratio $R_1/R_2>0.56$. For instance, taking $R_2-R_1=1$ cm (in order to meet the $\Delta Z/Z<1\%$ criterion with mechanical tolerances of only 0.001") and $R_2=2.3$ cm ($R_1/R_2=0.565$), the choice b=3 (L=2.89 cm) yields $Z_{max}=0.537$ cm$^2$/V/s (1.7 nanometers); $Z_{min}=0.00523$ cm$^2$/V/s. This covers the mass range from a few kilodalton to beyond 1 megadalton.

The previous considerations have been restricted to the case of cylindrical DMAs. However, they apply approximately also to axisymmetric DMAs with slowly converging walls. They also hold qualitatively in the case of rapidly converging walls.

An alternative means to reduce free stream turbulence proposed in this invention is to introduce a substantial (rather than a slight) contraction within the working section. This approach differs from earlier art, where the working section was unaccelerated and the large contraction was placed upstream from it. This key difference leads for diverse reasons to variations in performance between the two approaches.

We have discussed the advantages of a small sustained acceleration within the full working section for the purpose of avoiding turbulent transition. We have pointed to out that the large inlet trumpet of U.S. Pat. No. 5,869,831 placed upstream of the working section is very useful to delay transition in the case of plane or cylindrical electrodes. But such a large trumpet is not necessary for this purpose in DMAs with converging electrodes, because the slight contraction of the working section provides boundary layer stabilization even with a moderate level of free-stream turbulence. There is nonetheless an advantage of a large accelerating trumpet upstream of the working section, because the associated free-stream turbulence reduction decreases peak broadening associated to velocity fluctuations. The cost and inconvenience of a relatively large inlet section may in some special applications be desirable, such as, for instance, to achieve $\Delta Z/Z$ values even smaller than 1% in mechanically very perfect DMAs run at particularly large Reynolds numbers.

Larger angles of convergence allow shortening certain parts of the DMA, hence reducing their weight and cost, increasing mechanical perfection, decreasing ion losses by diffusion in the outlet line, etc. For instance, the throat preceding the sheath air exhaust must be placed at a certain distance downstream of the sampling slit. For cylindrical or plane electrodes, their surface must then incorporate relatively long concave and convex sections, or sudden changes of slope which are fluid-dynamically undesirable. For the modest angle of convergence shown in FIG. 1, the axial distance between the throat and the sampling slit is several times the optimal DMA length L*. It could evidently be substantially shorter with more rapidly converging electrodes. Similar considerations apply to the region upstream the inlet slit. In U.S. Pat. No. 5,869,831, the inlet trumpet is first concave and then convex, finishing in a direction parallel to the walls of the working section. The inlet trumpet is consequently rather long and heavy. Its length was decreased in the design of Herrmann by elimination of the initial concave part and by use of a conical inlet of relatively large angle (FIG. 2). However, the transition between this converging inlet and the non-converging working section must be gradual (therefore long) in order to avoid flow separation. The relatively long associated transition regions lead also to wide boundary layers at the aerosol inlet section, which precipitate transition. Most of these problems are eliminated by using a rapidly converging working section. If the inlet trumpet (small or large) has the same or a smaller angle of convergence than the working section, the transition between both can be relatively short or entirely absent. At the exhaust section the distance between the nozzle and the sampling slit can be made relatively short, since neither a straightening of the jet at the inlet of the exhaust chamber is needed, nor a change of curvature or slope immediately after the sampling slit.

From the point of view of reducing free-stream turbulence and hence controlling the associated peak broadening it may seem that an apparent disadvantage of accelerating through the working section (rather than prior to it) is that the beginning of the ion separation process occurs at a higher level of free-stream turbulence, while only the final stages of the analysis proceed in a more laminar environment. The advantage of U.S. Pat. No. 5,869,831 where the full analyzing region occurs at a small free stream turbulence level, is undeniable. However, this disadvantage of the present invention is partially offset by the advantages just discussed. Furthermore, the final stages of the ion motion through the working section have a much larger impact on peak broadening than the initial ones, so that this negative influence tends to be substantially smaller than would seem at first sight. This can be seen by treating beam broadening associated to free stream turbulence as if it were governed by the same rules as Brownian diffusion, though with an increased effective diffusion coefficient. The role of acceleration on Brownian broadening can be illustrated by the particular case of a two-dimensional DMA of planar walls converging at an angle $\alpha$. In this case, the analog of the quantity b introduced in (1–2) is the group $k=ZV/Q'$, where $Q'$ is still the flow rate per unit slit length, and, $\Delta Z/Z \sim (k+1/k)^{1/2}(b \sim L/\Delta$, where L and $\Delta$ are still the axial distance between inlet and outlet slits, and the distance between electrodes at the outlet section). $1/k=b_{ef}$ plays here the role of an effective b governing the increase of diffusive broadening above the minimum associated to the optimal geometry (k=1). For a two-dimensional DMA of planar walls converging at an angle $\alpha$ we may write:

$$bk=[e^{\alpha/k}-1]/(\alpha/k).$$

When $\alpha/k$ is small, this group tends to unity, so that the actual and diffusion DMA lengths coincide approximately. For values of k of order one (near optimal geometry) this corresponds to small angles of convergence. At large angles of convergence, however, b may be considerably larger than 1/k. For instance, at k=⅓ and a=45°, b=12.16. In other words, although a DMA with b=12 is relatively long and one would expect a high diffusive broadening, in reality a high convergence makes this broadening much smaller than for a cylinder, with $b_{ef}$ of only 3. In essence this means that most of the broadening action occurs over the region closest to the sampling slit (where the flow is more completely laminarized) rather than through [th]e more perturbed inlet region.

If a typical cylindrical DMA built according to U.S. Pat. No. 5,869,831 would have a trumpet inlet radius $R_0$=52 mm and cylindrical working sections with radii $R_2$=9 mm, $R_1$=4 mm, a typical DMA built according to the present invention would have the same inlet radius, and hence the same overall width. However, at the inlet slit it would have $R_2$=52/√6= 21.23 mm, $R_1$=0, with a modest contraction ratio very close to the total area contraction ratio of 6 used previously in the Vienna DMA between the last laminarization screen and the beginning of the working section (the inlet slit). Shortly downstream the inlet slit, the inner radius would rise rapidly to its final radius of 4 mm, while the outer radius would continue converging through the working section at the same rate as ahead of the inlet slit, or at an even larger rate. The effective level of laminarization would then be comparable in both configurations, as would the diameter and effectiveness of the laminarization screens, as well as the sheath gas exhaust section and associated pumping requirements. The new DMA would, however, be considerably shorter than that based on U.S. Pat. No. 5,869,831. This would allow lengthening in the present invention the inlet region prior to the aerosol injection slit, thereby further dissipating the already small level of turbulence generated at the inlet screens or surviving through them. The level of convergence downstream the inlet slit would then be higher than upstream, with a particularly intense flow acceleration level therefore helping stabilizing the mixing layer.

We have discussed the advantages of creating a throat downstream the aerosol sampling slit in order to decouple the laminar axisymmetric flow field needed in the working section from the generally highly perturbed turbulent and non-axi symmetric flow prevailing in the shath gas exhaust chamber. Earlier DMA models have sought that isolation by having high flow constrictions. We have used much smaller constrictions forced by the need to minimize pressure drop and maximize flow rate. In either case, even if the constriction isolates the mean flow in the sampling slit region from the sheath gas exhaust chamber, pressure fluctuations travel at the speed of sound, and can still propagate upstream against a subsonic flow. Hence, the intense fluctuations surely present in the sheath gas exhaust chamber can radiate upstream, thereby limiting resolution. This possibility is potentially most damaging at flow conditions able to excite acoustic resonances either in the exhaust chamber or the working section of the DMA. Such resonances have been observed in the Herrmann DMA described earlier in the vicinity of a critical Reynolds number, and lead to a serious deterioration of the instrument's resolution in a relatively wide range of flow rates about the critical. If the resonance is created within the exhaust chamber, its negative effects in the working section would be specially serious in low pressure drop designs due to their relatively small constriction. This acoustic radiation phenomenon has not been studied to any extent in DMAs, probably because it is not sufficiently intense to modify resolution under typical operating conditions, where $\Delta Z/Z$ is as high as 10 or 20%. Furthermore, typical DMA Reynolds numbers are small and associated acoustic noise in the exhaust chamber must be modest.

However, the very large Reynolds numbers of interest to this invention lead to substantially more intense acoustic fields, which can be heard very well, even when no resonance seems to be excited. The need for resolutions in the vicinity of 1% also makes the impact of small radiative effects potentially serious. This is a common problem in many flow systems, and can be alleviated by a variety of means, including geometrical and fluid dynamical design. In addition to these traditional schemes, the present invention includes the possibility to isolate completely the laminar working section from the acoustic radiation field from the inevitably turbulent sheath gas exhaust chamber by driving the flow to sonic conditions at the throat following the aerosol sampling slit.

Another embodiment of the present invention would use a high speed subsonic flow through the whole analyzing region including a moderate distance downstream the aerosol sampling slit. The flow would then be accelerated to sonic and slightly supersonic conditions through the nozzle throat and beyond it, and the supersonic region would isolate the working region of the DMA from acoustic radiation from the highly perturbed flow present further downstream. A slight contraction will make the flow sonic in the throat and slightly supersonic thereafter, precluding completely the entry of any pressure fluctuations from downstream the throat into the sensitive analyzing section.

What is claimed:

1. A method of separating charged particles or ions in a differential mobility analyzer, wherein a stream of charged particles or ions is introduced into an upstream portion of an analyzing region through an inlet slit or orifice and wherein a combination of a laminar flow field and an electrical field leads to ions of different mobilities separating in space, said method comprising the steps of:

(a) introducing a stream of charged particles or ions of various electrical mobilities into said analyzing region;

(b) laminarizing a flow of an ion-free sheath gas, and introducing said sheath gas into said differential mobility analyzer immediately upstream of said analyzing region;

(c) providing an electrical field in said analyzing region by a combination of electrodes and grids charged to various voltages and charging devices to maintain said electrodes and grids at said various voltages;

(d) sampling or collecting said separated particles or ions within a narrow range of electrical mobilities through at least one sampling or collector device, the last of which defines the exit of said analyzing region; and (e) minimizing flow resistance of the ion-free sheath as through the differential mobility analyzer by placing a diffuser downstream from the analyzing region.

2. A method according to claim 1, wherein the flow of the sheath gas is maintained within the analyzing region as a laminar flow by introducing a gradual reduction of the flow cross-section as the sheath gas moves downstream through said analyzing region.

3. A method according to claim 1, wherein said flow of said sheath gas is maintained as a laminar flow in an entry region where it meets said inlet stream of ions by reducing a cross section of said flow in a vicinity of said entry region to locally accelerate said flow.

4. A method according to claim 1, wherein said laminar flow is accelerated to a velocity above 100 m/s within said analyzing region.

5. A method according to claim 1, wherein the flow of the ion-free sheath gas is constricted by positioning a flow constriction or throat between the exit of the analyzing region and the inlet of the diffuser.

6. A method according to claim 5, wherein the exhaust chamber of the differential mobility analyzer is positioned downstream of the flow constrictor and is further connected to at least three symmetrically distributed exhaust lines.

7. A method according to claim 1, wherein one or more of said electrodes or grids are supported upstream of the analyzing region.

8. A method according to claim 1, wherein said stream of charged particles or ions is produced by ionizing preexisting volatile substances upstream of said inlet slit.

9. A method according to claim 8, wherein said particles or ions are charged with a radioactive source.

10. A method according to claim 9, wherein said radioactive source is selected from the group consisting of $^{63}$Ni, $^{210}$Po, and other alpha and beta emitters.

11. A method according to claim 8, wherein said particles or ions are charged using electrospraying.

12. A method according to claim 1, wherein said analyzing region is isolated from downstream acoustic radiation by causing flow in a region between the at least one collector device and said diffuser to reach the speed of sound.

13. A method according to claim 1, where at least two of said electrodes or grids are axisymmetric within said analyzing region, with geometrical errors smaller than 0.5% of the smallest distance encountered in said analyzing region between said at least two electrodes or grids.

14. A method according to claim 13, where at least two of said electrodes or grids are axisymmetric within said analyzing region, with geometrical errors smaller than 0.25% of the smallest distance encountered in said analyzing region between said at least two electrodes or grids.

15. A method according to claim 1, wherein resolution of said differential mobility analyzer is increased by designing an aerosol injection chamber upstream of said inlet slit such that pressure drop for the flow of said stream of charged particles or ions along a length of the inlet slit is substantially smaller than for its flow across the inlet slit.

16. A method according to claim 1 wherein said electrical potential applied to at least one of said electrodes in electrical contact with said inlet slit and said electrical potential applied to at least one of said sampling or collector, electrodes are substantially the same.

17. A method according to claim 1, wherein said one or more collector devices comprise a plurality of collector devices.

18. A differential mobility analyzer for separating ions and charged particles suspended in a mixture comprising:

means to provide a laminar flow of ion-free sheath gas into an upstream end of an analyzing region;

ion supply means for introducing said ions and charged particles into said analyzing region;

at least two electrodes or grids charged to suitable potentials to create an electric field within said analyzing region;

whereby said ions are separated in space by combined action of the electric field and the flow of sheath gas;

at least one sampling or collecting device, wherein ions of a desired mobility are sampled or collected;

power supply means to charge said at least two electrodes or grids to said potentials;

means for maintaining said laminar flow within said analyzing region; and means for minimizing flow resistance of the ion-free sheath gas by placing a diffuser downstream from the analyzing region.

19. The differential mobility analyzer as recited in claim 18, wherein the ion supply means for introducing said ions and charged particles into said analyzing chamber comprise an inlet chamber (12), communicating with the analyzing region via an inlet slit or orifice (4).

20. The differential mobility analyzer as recited in 19, wherein a downstream end of the means to provide a laminar flow of ion-free sheath gas into the upstream end of the analyzing region is converging until it meets said inlet slit or orifice (4).

21. The differential mobility analyzer of claim 19, wherein said means for maintaining said laminar flow within said analyzing region comprise a gradual reduction of flow cross section as said flow moves downstream through the analyzing region.

22. The differential mobility analyzer of claim 19, wherein said means for maintaining said laminar flow within said analyzing region includes means of local acceleration of said flow in an entry region of said analyzing region at a point where said particle-free sheath gas meets said inlet stream of particles or ions.

23. The differential mobility analyzer of claim 22, wherein said means of local acceleration comprise reducing the cross section of the flow.

24. The differential mobility analyzer of claim 18, wherein the exhaust chamber is connected to a downstream pumping chamber through at least two symmetrically placed exhaust tubes.

25. The differential mobility analyzer of claim 18, wherein velocity of said laminar flow in at least one point of said analyzing chamber exceeds 100 m/s.

26. The differential mobility analyzer as recited in claim 18, wherein one or more of said electrodes are supported upstream of the analyzing region.

27. The differential mobility analyzer of claim 18, wherein one of said at least two electrodes has its leading edge downstream of said inlet slit so as to minimize diffusion broadening.

28. The differential mobility analyzer as recited in claim 18, wherein the means to provide a laminar flow of ion-free sheath gas into the upstream end of an analyzing region comprise passing said sheath gas through at least one filter and at least one screen, and then accelerating it through a converging region.

29. The differential mobility analyzer as recited in claim 28, wherein the screen most downstream among said at least one screen makes the flow turbulent by operating above a critical Reynolds number necessary to produce screen turbulence, and wherein this turbulent flow is subsequently relaminarized in said converging region.

30. The differential mobility analyzer of claim 18, wherein said stream of charged particles or ions is produced by ionizing preexisting volatile substances in a space located upstream of said inlet slit by suitable charging means.

31. The differential mobility analyzer of claim 30, wherein said charging means comprise a radioactive source.

32. The differential mobility analyzer of claim 31, wherein said radioactive source is selected from the group consisting of $^{63}$Ni, $^{210}$Po and other alpha or beta emitters.

33. The differential mobility analyzer of claim 32, wherein said charging means comprises an electrospray source.

34. The differential mobility analyzer of claim 18, wherein said analyzing region is isolated from downstream acoustic radiation by causing the flow to reach the speed of sound in a region between said at least one collector device and a diffuser.

35. The differential mobility analyzer of claim 18, wherein at least two of said electrodes or grids are axisymmetric within said analyzing region, with geometrical errors smaller than 0.5% of the smallest distance encountered in said analyzing region between said at least two electrodes or grids.

36. The differential mobility analyzer of claim 35, wherein at least two of said electrodes or grids are axisymmetric within said analyzing region, with geometrical errors smaller than 0.25% of the smallest distance encountered in said analyzing region between said at least two electrodes or grids.

37. The differential mobility analyzer of claim 18, wherein resolution is increased by designing an aerosol injection chamber upstream of said inlet slit such that pressure drop for the flow of said stream of charged particles or ions along a length of the inlet slit is substantially smaller than for its flow across the inlet slit.

38. The differential mobility analyzer as recited in claim 18, wherein said electrical potential applied to at least one of said electrodes in electrical contact with said inlet slit and said electrical potential applied to at least one of said sampling or collector electrodes are substantially the same.

39. The differential mobility analyzer as recited in claim 18, wherein said one or more collector devices comprise a plurality of collector devices.

40. A method of separating charged particles or ions in a differential mobility analyzer, wherein a stream of charged particles or ions is introduced into an upstream portion of an analyzing region through an inlet slit or orifice and wherein a combination of a laminar flow field and an electrical field leads to ions of different mobilities separating in space, said method comprising the steps of:

(a) introducing a stream of charged particles or ions of various electrical mobilities into said analyzing region;

(b) laminarizing a flow of an ion-free sheath gas, and introducing said sheath gas into said differential mobility analyzer immediately upstream of said analyzing region;

(c) providing an electrical field in said analyzing region by a combination of electrodes and grids charged to various voltages and charging devices to maintain said electrodes and grids at said various voltages;

(d) sampling or collecting said separated particles or ions within a narrow range of electrical mobilities through at least one sampling or collector device, the last of which defines the exit of said analyzing region; and (e) minimizing tendency towards turbulent transition through the differential mobility analyzer by introducing a gradual reduction of the flow cross-section as the sheath gas moves downstream through the analyzing region.

41. A method according to claim 40, wherein said flow of said sheath gas is maintained as a laminar flow in an entry region where it meets said inlet stream of ions by reducing a cross section of said flow in said entry region to locally accelerate said flow.

42. A method according to claim 40, wherein the flow of the ion-free sheath gas is constricted by positioning a flow constrictor downstream of the exit of the analyzing region followed by a diffuser.

43. A method according to claim 42, wherein the exhaust chamber of the differential mobility analyzer is positioned downstream of the flow constrictor and is further connected to at least three symmetrically distributed exhaust lines.

44. A method according to claim 40, wherein one or more of the electrodes or grids are supported upstream of the analyzing region.

45. A method according to claim 40, wherein said stream of charged particles or ions is produced by ionizing preexisting volatile substances upstream of said inlet slit.

46. A method according to claim 42, wherein said analyzing region is isolated from downstream acoustic radiation by causing flow in a region between the at least one collector device and the diffuser to reach the speed of sound.

47. A method according to claim 40, wherein said electrical potential applied to at least one of said electrodes in electrical contact with said inlet slit and said electrical potential applied to at least one of said sampling or collector electrodes are substantially the same.

48. A method according to claim 40, wherein said one or more collector devices comprise a plurality of collector devices.

49. A method of separating charged particles or ions in a differential mobility analyzer, wherein a stream of charged particles or ions is introduced into an upstream portion of an analyzing region through an inlet slit or orifice and wherein a combination of a laminar flow field and an electrical field leads to ions of different mobilities separating in space, said method comprising the steps of:
   (a) introducing a stream of charged particles or ions of various electrical mobilities into said analyzing region;
   (b) laminarizing a flow of an ion-free sheath gas, and introducing said sheath gas into said differential mobility analyzer immediately upstream of said analyzing region, wherein said laminar flow has a Reynolds number in excess of 2000;
   (c) providing an electrical field in said analyzing region by a combination of electrodes and grids charged to various voltages and charging devices to maintain said electrodes and grids at said various voltages;
   (d) sampling or collecting said separated particles or ions within a narrow range of electrical mobilities through at least one sampling or collector device, the last of which defines the exit of said analyzing region; and
   (e) minimizing upstream propagation of flow disturbances and flow asymmetry of the ion-free sheath gas originating in an exhaust system of the differential mobility analyzer, and minimizing flow resistance of the ion-free sheath gas through the differential mobility analyzer by supporting one or more of said electrodes or grids upstream of the analyzing region.

50. A method according to claim 49, wherein the flow of the sheath gas is maintained within the analyzing region as a laminar flow by introducing a gradual reduction of the flow cross-section as the sheath gas moves downstream through said analyzing region.

51. A method according to claim 49, wherein said flow of said sheath gas is maintained as a laminar flow in an entry region where it meets said, inlet stream of ions by reducing a cross section of said flow in said entry region to locally accelerate said flow.

52. A method according to claim 49, wherein the flow of the ion-free sheath gas is constricted, by positioning a flow constrictor downstream of the exit of the analyzing region followed by a diffuser.

53. A method according to claim 49, wherein said stream of charged particles or ions is produced by ionizing preexisting volatile substances upstream of said inlet slit.

54. A method according to claim 52, wherein said analyzing region is isolated from downstream acoustic radiation by causing flow in a region between the at least one collector device and said diffuser to reach the speed of sound.

55. A method according to claim 49, wherein said electrical potential applied to at least one of said electrodes in electrical contact with said inlet slit, and said electrical potential applied to at least one of said sampling or collector electrodes are substantially the same.

56. A method according to claim 49, wherein said one or more collector devices comprise a plurality of collector devices.

57. A differential mobility analyzer for separating ions and charged particles suspended in a mixture comprising:
   means to provide a laminar flow of ion-free sheath gas into an upstream end of an analyzing region;
   ion supply means for introducing said ions and charged particles into said analyzing region;
   at least two electrodes charged to suitable potentials to create an electric field within said analyzing region;
   whereby said ions are separated in space by combined action of the electric field and the flow of sheath gas;
   at least one sampling or collecting device, wherein ions of a desired mobility are sampled or collected;
   power supply means to charge said at least two electrodes to said potentials;
   means for maintaining said laminar flow within said analyzing region; and
   means for minimizing tendency towards turbulent transition comprising introducing a gradual reduction of the flow cross-section as the flow moves downstream through the analyzing region.

58. The differential mobility analyzer as recited in claim 57, wherein the ion supply means for introducing said ions and charged particles into said analyzing chamber comprise an inlet chamber (12), communicating with the analyzing region via an inlet slit or orifice (4).

59. The differential mobility analyzer as recited in 58, wherein a downstream end of the means to provide a laminar flow of ion-free sheath gas into the upstream end of the analyzing region is converging until it meets said inlet slit or orifice (4).

60. The differential mobility analyzer of claim 58, wherein said means for maintaining said laminar flow within said analyzing region includes means of local acceleration of said flow in an entry region of said analyzing region at a point where said particle-free sheath gas meets said inlet stream of particles or ions.

61. The differential mobility analyzer of claim 57, further comprising a flow constrictor positioned downstream of an exit of the analyzing region followed by a diffuser.

62. The differential mobility analyzer of claim 61, wherein the exhaust chamber is positioned downstream of the flow constrictor and is connected to a downstream pumping chamber through at least two symmetrically placed exhaust tubes.

63. The differential mobility analyzer as recited in claim 57, wherein one or more of said electrodes or grids are supported upstream of the analyzing region.

64. The differential mobility analyzer as recited in claim 57, wherein one of said at least two electrodes has its leading edge downstream of said inlet slit so as to minimize diffusion broadening.

65. The differential mobility analyzer as recited in claim 57, wherein the means to provide a laminar flow of ion-free sheath gas into the upstream end of an analyzing region comprise passing said sheath gas through at least one filter and at least one screen, and then accelerating it through a converging region.

66. The differential mobility analyzer as recited in claim 65, wherein the screen most downstream among said at least one screen makes the flow turbulent by operating above a critical Reynolds number necessary to produce screen turbulence, and wherein this turbulent flow is subsequently relaminarized in said converging region.

67. The differential mobility analyzer of claim 57, wherein said stream of charged particles or ions is produced by ionizing preexisting volatile substances in a space located upstream of said inlet slit by suitable charging means.

68. The differential mobility analyzer of claim 61, wherein said analyzing region is isolated from downstream acoustic radiation by causing the flow to reach the speed of sound in a region between said at least one collector device and the diffuser.

69. The differential mobility analyzer as recited in claim 57, wherein said electrical potential applied to at least one of said electrodes in electrical contact with said inlet slit, and said electrical potential applied to at least one of said sampling or collector electrodes are substantially the same.

70. The differential mobility analyzer as recited in claim 57, wherein said one or more collector devices comprise a plurality of collector devices.

71. A differential mobility analyzer for separating ions, and charged particles suspended in a mixture comprising:
  means to provide a laminar flow of ion-free sheath gas into an upstream end of an analyzing region at a Reynolds number in excess of 2000;
  ion supply means for introducing said ions and charged particles into said analyzing region;
  at least two electrodes or grids charged to suitable potentials to create an electric field within said analyzing region;
  whereby said ions are separated in space by combined action of the electric field and the flow of sheath gas;
  at least one sampling or collecting device, wherein ions of a desired mobility are sampled or collected;
  power supply means to charge said at least two electrodes or grids to said potentials;
  means for maintaining said laminar flow within said analyzing region; and
  means for minimizing upstream propagation of flow disturbances, flow asymmetry, and flow resistance through the differential mobility analyzer, wherein said means comprise supporting one or more of said electrodes or grids upstream of the analyzing region.

72. The differential mobility analyzer as recited in claim 71, wherein the ion supply means for introducing said ions and charged particles into said analyzing chamber comprise an inlet chamber (12), communicating with the analyzing region via an inlet slit or orifice (4).

73. The differential mobility analyzer as recited in 72, wherein a downstream end of the means to provide a laminar flow of ion-free sheath gas into the upstream end of the analyzing region is converging until it meets said inlet slit or orifice (4).

74. The differential mobility analyzer of claim 72, wherein said means for maintaining said laminar flow within said analyzing region comprise a gradual reduction of flow cross section as said flow moves downstream through the analyzing region.

75. The differential mobility analyzer of claim 72, wherein said means for maintaining said laminar flow within said analyzing region includes means of local acceleration of said flow in an entry region of said analyzing region at a point where said particle-free sheath gas meets said inlet stream of particles or ions.

76. The differential mobility analyzer of claim 75, wherein said means of local acceleration comprise reducing the cross section of the flow.

77. The differential mobility analyzer of claim 71, further comprising a diffuser following the analyzing region.

78. The differential mobility analyzer of claim 77, wherein the exhaust chamber is positioned downstream of the flow constrictor and is connected to a downstream pumping chamber through at least two symmetrically placed exhaust tubes.

79. The differential mobility analyzer as recited in claim 71, wherein said electrical potential applied to at least one of said electrodes in electrical contact with said inlet slit, and said electrical potential applied to at least one of said sampling or collector electrodes are substantially the same.

80. The differential mobility analyzer as recited in claim 71, wherein said one or more collector devices comprise a plurality of collector devices.

81. The differential mobility analyzer as recited in claim 71, wherein the screen most downstream among said at least one screen makes the flow turbulent by operating above a critical Reynolds number necessary to produce screen turbulence, and wherein this turbulent flow is subsequently relaminarized in said converging region.

82. The differential mobility analyzer of claim 71, wherein said stream of charged particles or ions is produced by ionizing preexisting volatile substances in a space located upstream of said inlet slit by suitable charging means.

83. The differential mobility analyzer of claim 77, wherein said analyzing region is isolated from downstream acoustic radiation by causing the flow to reach the speed of sound in a region between said at least one collector device and the diffuser.

* * * * *